United States Patent
Kawashima et al.

Patent Number: 5,946,085
Date of Patent: Aug. 31, 1999

[54] DIELECTRIC DISPERSION DETERMINING METHOD IN TERAHERTZ REGION USING FEMTOSECOND ULTRASHORT VISIBLE OPTICAL PULSE

[75] Inventors: Hitoshi Kawashima; Fumio Sasaki; Shunsuke Kobayashi; Toshiro Tani, all of Tsukuba, Japan

[73] Assignee: Agency of Industrial Science and Technology, Tokyo, Japan

[21] Appl. No.: 09/037,424

[22] Filed: Mar. 10, 1998

[30] Foreign Application Priority Data

Mar. 11, 1997 [JP] Japan ............................ 9-056139

[51] Int. Cl.⁶ .................................. G01N 21/41
[52] U.S. Cl. ..................................... 356/128
[58] Field of Search ........................ 356/128–137, 356/345, 73

[56] References Cited

U.S. PATENT DOCUMENTS 5,604,581  2/1997  Liu et al. .................... 356/73

Primary Examiner—Robert H. Kim
Assistant Examiner—Amanda Merlino
Attorney, Agent, or Firm—Fleshner & Kim

[57] ABSTRACT

A dielectric dispersion determining method applying a transient grating method. The transient response of a sample is observed by the transient grating method using a femtosecond ultrashort visible optical pulse. A vibrational waveform $b(t)$ is determined such that its square $b(t)^2$ replicates vibrational components observed in the transient response. The vibrational waveform $b(t)$ is converted into $b(\omega)$ through the Fourier transform. The dielectric constant $\epsilon(\omega)$ is obtained by substituting the converted value for $b(\omega)/\omega^2$ on the right-hand side of the following equation (1) derived from Maxwell's equations. The dielectric constant and/or refraction index can be directly obtained from the transient response to the femtosecond ultrashort visible optical pulse without passing through the dispersion relation which leaves some ambiguity in its definition.

$$\varepsilon(\omega) = \frac{C^2 q_0^2}{\omega^2} \cdot \left\{ 1 - \left( \frac{b(\omega)}{\omega^2} \right)^{-1} \right\} \quad (1)$$

5 Claims, 2 Drawing Sheets

DIELECTRIC DISPERSION DETERMINING METHOD IN TERAHERTZ REGION USING FEMTOSECOND ULTRASHORT VISIBLE OPTICAL PULSE

This application is based on patent application Ser. No. 056,139/1997 filed Mar. 11, 1997 in Japan, the content of which is incorporated hereinto by reference.

BACKGROUND OF THE INVENTION

1. FIELD OF THE INVENTION

The present invention relates to a dielectric dispersion determining method in a terahertz region using a femtosecond ultrashort visible optical pulse for determining a dielectric constant (and/or refractive index) of a nonlinear optical crystal in a terahertz region with a femtosecond ultrashort visible optical pulse.

2. DESCRIPTION OF THE RELATED ART

In a wavelength conversion technique called parametric conversion using a nonlinear optical crystal, visible rays are converted into far infrared rays with frequencies over the range of 0.1–100 terahertz (wavelengths in the range of 3 mm to 3 micron). Dielectric constants (and refractive indices) in the far infrared region are important optical constants indicating the performance of crystals in searching for a new crystal system or in establishing phase matching conditions providing most effective conversion.

Conventionally, the terahertz region dielectric constants (refractive indices) are obtained by measuring reflectances or transmittances using a far infrared optical measuring system. Such a system, however, requires a light source like a far infrared lamp, an optical waveguide device or optical focusing system, and a detector, which are special devices and thus expensive. In particular, the detector needs delicate handling such as cooling with cryogen.

Such a direct method, however, is not essential in obtaining the dielectric constants (refractive indices) in the far infrared region. For example, they can be acquired in principle by reading with visible rays changes induced by infrared rays through electrooptic effect in the refraction area in the visible region. This becomes feasible by a method of solid state measurement called "time domain measurement" growing with the progress in the femtosecond ($10^{-15}$ second) ultrashort visible optical pulse generating technique over the last 15 years.

In a transient grating method, one of fundamental measuring techniques using a ultrashort visible optical pulse, two ultrashort visible optical pulses are crossed in a sample, thereby generating sample excitation with a spatially periodic structure, that is, a grating. A third ultrashort pulse applied thereto will be diffracted by the grating. Thus, changes of the grating with time can be obtained by recording the intensity of the diffracted light with varying the incident time of the third ultrashort pulse through a delay optical path. A transient response thus obtained has not been used for determining the dielectric constant (refractive index) because the conventional interpretation thereof places emphasis on the dependence of the infrared ray frequency on the wavelength (grating constant).

Although the conventional interpretation of the transient response in the transient grating method places emphasis on the dependence (dispersion relation) of the infrared rays on the wavelength (grating constant), an ambiguity in the definition of the dispersion relation makes it difficult to determine the dielectric constant (and/or refractive index) based on the dispersion relation.

SUMMARY OF THE INVENTION

It is, therefore, an object of the present invention to provide a dielectric dispersion determining method in a terahertz region capable of obtaining a dielectric constant and/or refractive index directly from the transient response to a femtosecond ultrashort visible optical pulse without using the dispersion relation having an ambiguity in its definition.

There is provided a dielectric dispersion determining method in a terahertz region, comprising the steps of:

applying a transient grating method using a femtosecond visible optical pulse to a nonlinear optical crystal; and applying Fourier transform to a transient response induced by the ultrashort visible optical pulse, thereby determining a dielectric constant and/or refractive index of the nonlinear optical crystal in the terahertz region.

Here, the dielectric dispersion determining method may comprise:

the first step of detecting the transient response of a grating induced by the ultrashort visible optical pulse by applying the transient grating method to a sample;

the second step of determining a vibrational waveform $b(t)$ such that its square $b(t)^2$ replicates vibrational components of the transient response obtained in the first step;

the third step of applying the Fourier transform to the vibrational waveform $b(t)$ to obtain $b(\omega)$ at frequency $\omega$; and the fourth step of obtaining dependence of the dielectric constant $\epsilon(\omega)$ on the frequency $\omega$ by substituting the $b(\omega)$ obtained for $b(\omega)$ in equation (1) derived from Maxwell's equations.

$$\varepsilon(\omega) = \frac{c^2 q_0^2}{\omega^2} \cdot \left\{ 1 - \left(\frac{b(\omega)}{\omega^2}\right)^{-1} \right\}, \qquad (1)$$

where c is light speed, and $q_0$ is a reciprocal of a spatial frequency of the diffraction grating.

The dielectric dispersion determining method may further comprise the fifth step of obtaining the refractive index of the sample from a root of the dependence of the dielectric constant $\epsilon(\omega)$ on the frequency obtained in the fourth step.

The transient grating method applied to the sample in the first step may generate a sample excitation with a spatially periodic structure, that is, a grating, by crossing two ultrashort visible optical pulses in the sample; may launch a third ultrashort visible optical pulse into the grating to generate diffracted light; and may output changes of the grating with time by recording intensity of the diffracted light with varying the incident time of the third ultrashort pulse through a delay optical path.

The above and other objects, effects, features and advantages of the present invention will become more apparent from the following description of embodiments thereof taken in conjunction with the accompanying drawings.

DETAILED DESCRIPTION OF PREFERRED EMBODIMENTS

Figure 1:
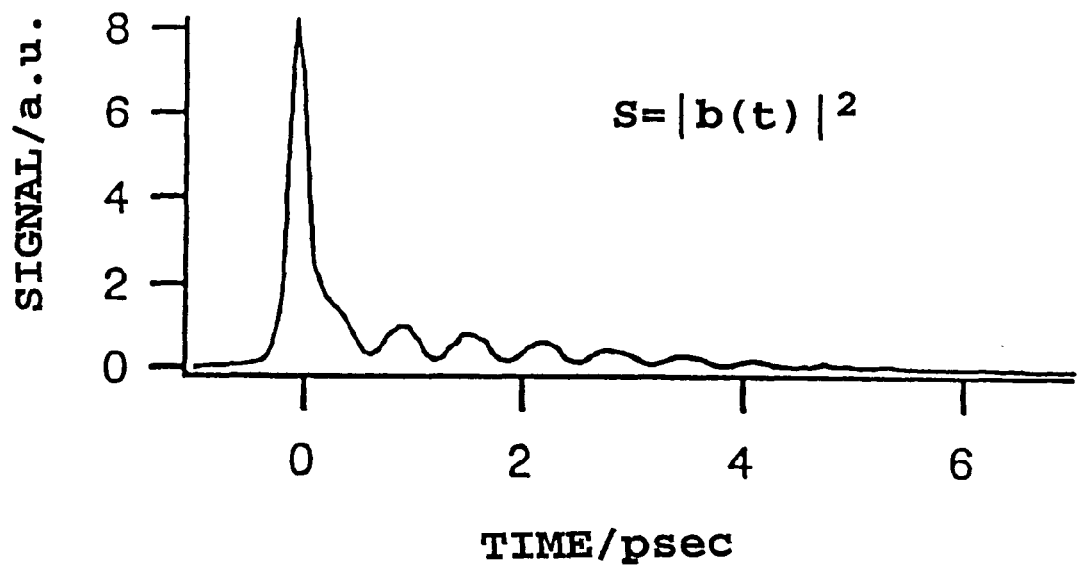
FIG. 1 is a graph illustrating an actually observed response in a transient grating method using $LiTaO_3$ as a sample in an embodiment in accordance with the present invention.

The present invention will now be described with reference to the accompanying drawings.

In order to solve the problem of the foregoing conventional technique, the present invention derives the following equation (1) from Maxwell's equations.

$$\varepsilon(\omega) = \frac{C^2 q_0^2}{\omega^2} \cdot \left\{ 1 - \left( \frac{b(\omega)}{\omega^2} \right)^{-1} \right\}, \quad (1)$$

where $\omega$ is the frequency, $\epsilon(\omega)$ on the left-hand side is the dielectric constant at the frequency $\omega$, c on the right-hand side is the speed of light, $q_0$ is a reciprocal of the spatial frequency of a diffraction grating, and $b(\omega)$ is the Fourier transform of the transient response b(t) of the grating induced by a ultrashort visible optical pulse.

Equation (1) indicates that the dielectric constant $\epsilon(\omega)$ is derived from the Fourier transform of the transient response observed in an experiment. The refractive index is obtained as $\epsilon(\omega)^{1/2}$, i. e., the root of the dielectric constant.

The optical system employed in the present invention is less expensive and simpler than the conventional far infrared optical measuring system because it uses the visible optical pulse in the transient grating method. In addition, the dependence of the dielectric constant on the frequency can be obtained over the wide range from a direct current to a terahertz region in the present invention. Furthermore, the upper limit of the frequency is determined by the reciprocal of the width of the visible optical pulse used, and is free from time response characteristics of an optical detector. For example, when the width of the visible optical pulse used is 10 femtoseconds, the upper limit of the frequency extends up to 100 terahertz.

The following is an example of a procedure for deriving the terahertz dielectric constant from the transient response induced by the ultrashort visible optical pulse.

(1) First, the response of a sample is detected by the transient grating method employing a well known optical system used in the conventional transient grating method. Specifically, two ultrashort visible optical pulses are crossed in the sample to generate the sample excitation with a spatially periodic structure, that is, a grating. A third ultrashort visible optical pulse launched thereinto is diffracted. The intensity of the diffracted light is recorded with varying the incident time of the third ultrashort pulse through a delay optical path, thereby outputting changes of the grating with time, that is, the response characteristics.

(2) The oscillatory waveform b(t) is determined such that its square b(t)$^2$ replicates the oscillatory components observed in the response characteristics.

(3) The oscillatory waveform b(t) is subjected to the Fourier transform to obtain $b(\omega)$.

(4) Substituting $\epsilon(\omega)$ into the right-hand side of equation (1) yields on its left-hand side the dependence of the dielectric constant $\epsilon(\omega)$ on the frequency because all the remaining quantities on the right-hand side are known. The refractive index is obtained as $\epsilon(\omega)^{1/2}$, i. e., the root of the dielectric constant.

As a specific embodiment of the present invention, the dependence of the dielectric constant on the frequency was obtained over the frequency range from the direct current to five terahertz using $LiTaO_3$ as a sample.

First, the response of the sample was observed by the transient grating method employing a well known optical system used in the conventional transient grating method. It used as its light source a ultrashort visible optical pulse with a width of 200 femtoseconds, for example. The calculation processing was carried out by a common personal computer. FIG. 1 illustrates the square S=|b(t)|$^2$ of the response characteristic b(t) actually observed in the transient grating method using $LiTaO_3$ as a sample.

Figure 2:
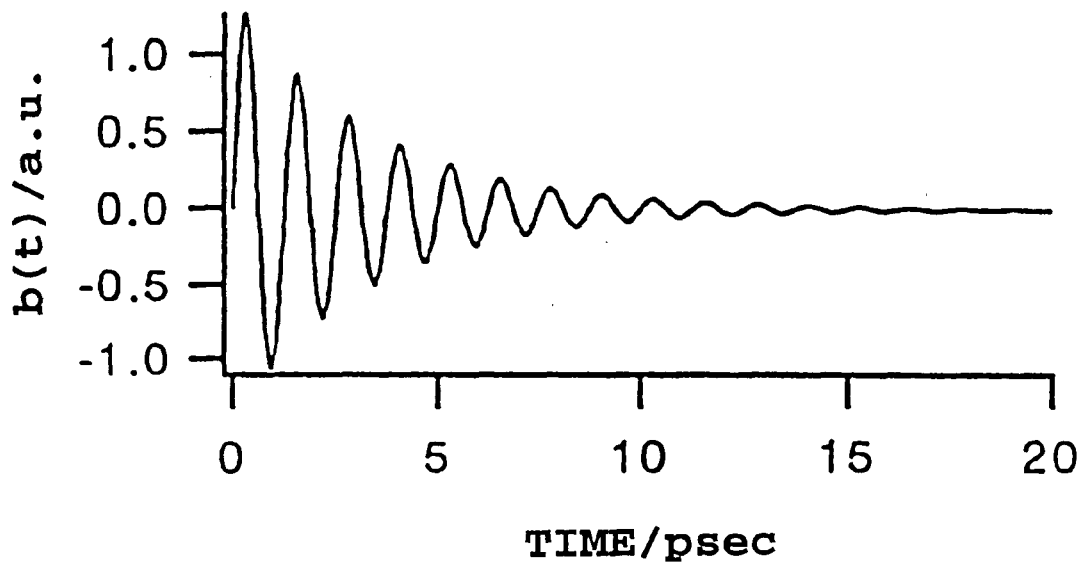
FIG. 2 is a graph illustrating an oscillatory waveform $b(t)$ determined such that its square equals the oscillatory components of the waveform in FIG. 1.

Next, the vibrational waveform b(t) was determined such that its square b(t)$^2$ replicated the vibrational components observed in the response characteristics. The vibrational waveform as illustrated in FIG. 2 represents b(t) determined such that its square agrees with the vibrational components of FIG. 1.

Figure 3:
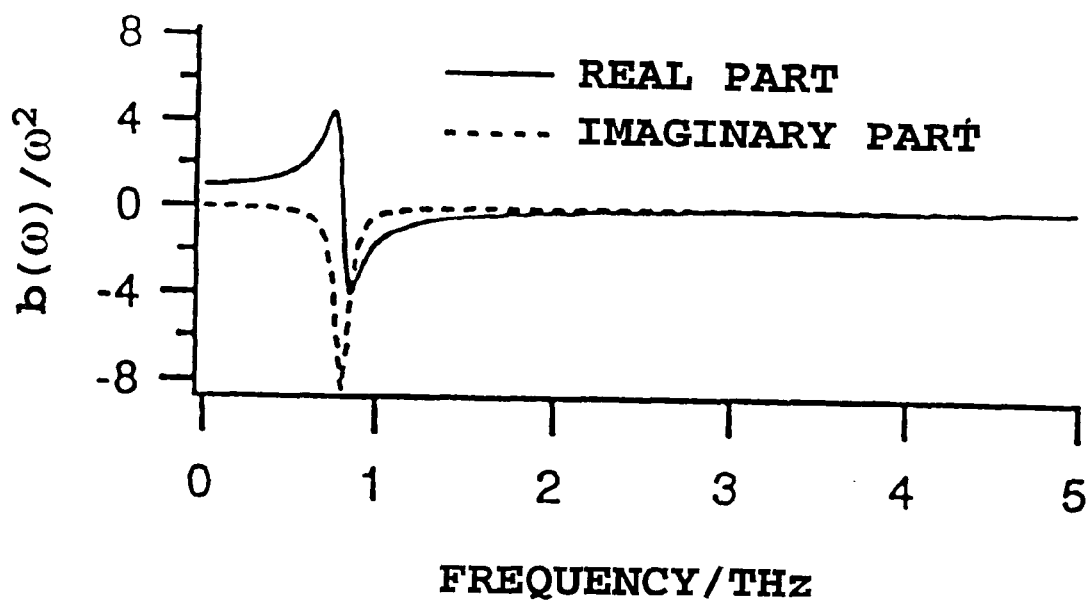
FIG. 3 is a graph illustrating a result obtained by dividing the Fourier transform $b(\omega)$ of $b(t)$ of FIG. 2 by the square of the frequency $\omega$.

Subsequently, the vibrational waveform b(t) was subjected to the Fourier transform to obtain $b(\omega)$. FIG. 3 illustrates $b(\omega)$ divided by the square of the vibration frequency $\omega$, in which a solid curve denotes its real part, and a broken curve denotes its imaginary part.

Figure 4:
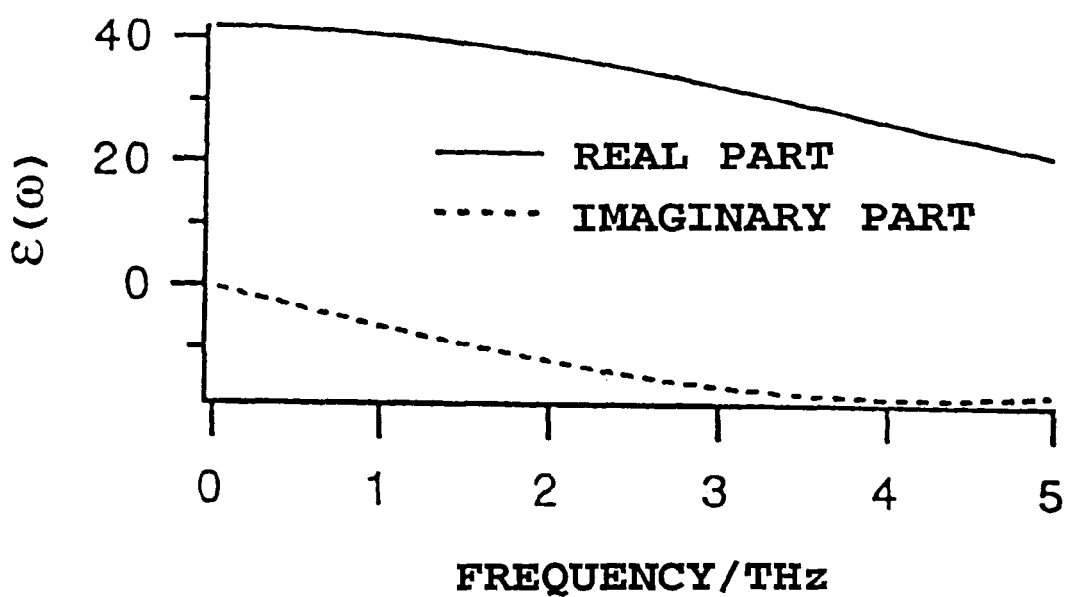
FIG. 4 is a graph illustrating the dependence of the dielectric constant on the frequency.

Finally, substituting $b(\omega)/\omega^2$ into the right-hand side of equation (1) yielded the dielectric constant $\epsilon(\omega)$. The spatial frequency of the diffraction grating was 1080 cm$^{-1}$. FIG. 4 illustrates the dependence of the dielectric constant $\epsilon(\omega)$ on the frequency, in which a solid curve denotes its real part, and a broken curve denotes its imaginary part.

As described above, the dielectric constant (and/or refractive index) determining method in accordance with the present invention provides a procedure for deriving the dielectric constant in the terahertz region from the transient response induced by the ultrashort visible optical pulse. As a result, the dielectric constant (and/or refractive index) of a nonlinear optical crystal in the terahertz region can be determined without using the optical system for the infrared rays in the present invention.

The present invention has been described in detail with respect to preferred embodiments, and it will now be apparent from the foregoing to those skilled in the art that changes and modifications may be made without departing from the present invention in its broader aspects, and it is the intention, therefore, in the appended claims to cover all such changes and modifications as fall within the true spirit of the present invention.

What is claimed is:

1. A dielectric dispersion determining method in a terahertz region, comprising the steps of:
    applying a transient grating method using a ultrashort visible optical pulse to a nonlinear optical crystal; and
    applying Fourier transform to a transient response induced by said ultrashort visible optical pulse, thereby determining a dielectric constant and/or refractive index of said nonlinear optical crystal in the terahertz region.

2. The dielectric dispersion determining method as claimed in claim 1, comprising:
    a first step of detecting the transient response of a grating induced by the ultrashort visible optical pulse by applying the transient grating method to a sample;
    a second step of determining a vibrational waveform b(t) such that its square b(t)$^2$ replicates vibrational components of said transient response obtained in the first step;
    a third step of applying the Fourier transform to said vibrational waveform b(t) to obtain $b(\omega)$ at frequency $\omega$; and
    a fourth step of obtaining dependence of the dielectric constant $\epsilon(\omega)$ on the frequency $\omega$ by substituting the b(ω) obtained for b(ω) in equation (1) derived from Maxwell's equations, $$\varepsilon(\omega) = \frac{c^2 q_0^2}{\omega^2} \cdot \left\{ 1 - \left( \frac{b(\omega)}{\omega^2} \right)^{-1} \right\}, \quad (1)$$

where c is light speed, and $q_0$ is a reciprocal of a spatial frequency of the diffraction grating.

3. The dielectric dispersion determining method as claimed in claim 2, further comprising a fifth step of obtaining the refractive index of said sample from a root of the dependence of said dielectric constant $\epsilon(\omega)$ on the frequency obtained in the fourth step.

4. The dielectric dispersion determining method as claimed in claim 2, wherein said transient grating method applied to said sample in the first step generates a sample excitation with a spatially periodic structure, that is, a grating, by crossing two ultrashort visible optical pulses in the sample; launches a third ultrashort visible optical pulse into said grating to generate diffracted light; and outputs changes of said grating with time by recording intensity of the diffracted light while varying the incident time of the third ultrashort pulse through a delay optical path.

5. The dielectric dispersion determining method as claimed in claim 3, wherein said transient grating method applied to said sample in the first step generates a sample excitation with a spatially periodic structure, that is, a grating, by crossing two ultrashort visible optical pulses in the sample; launches a third ultrashort visible optical pulse into said grating to generate diffracted light; and outputs changes of said grating with time by recording intensity of the diffracted light with varying the incident time of the third ultrashort pulse through a delay optical path.

* * * * *